(12) United States Patent
Heimberg

(10) Patent No.: US 6,398,281 B1
(45) Date of Patent: Jun. 4, 2002

(54) LID GRIPPING DEVICE

(75) Inventor: Wolfgang Heimberg, Ebersberg (DE)

(73) Assignee: MWG Biotech AG, Ebersberg (DE)

(*) Notice: Subject to any disclaimer, the term of this patent is extended or adjusted under 35 U.S.C. 154(b) by 0 days.

(21) Appl. No.: 09/223,295

(22) Filed: Dec. 30, 1998

(30) Foreign Application Priority Data

Jan. 15, 1998 (DE) .................................. 198 01 178

(51) Int. Cl.⁷ .............................. B25J 13/08; B25J 15/08
(52) U.S. Cl. ........................ 294/88; 294/100; 294/907; 901/46
(58) Field of Search ................... 294/88, 100, 86.14, 294/86.19, 86.28, 86.3, 86.4, 116, 907; 279/4.02, 4.08, 43, 46.3; 901/36, 46

(56) References Cited

U.S. PATENT DOCUMENTS

| | | | |
|---|---|---|---|
| 2,507,127 A | * 5/1950 | True | 294/88 |
| 4,320,914 A | * 3/1982 | Simon | 294/88 |
| 4,552,278 A | 11/1985 | Romanauskas | 215/277 |
| 4,830,832 A | 5/1989 | Arpagaus et al. | 422/65 |
| 4,911,490 A | * 3/1990 | Akagawa | 294/116 |
| 4,967,604 A | 11/1990 | Arpagaus et al. | 73/864.13 |
| 5,201,838 A | * 4/1993 | Roudaut | 294/88 |
| 5,775,755 A | * 7/1998 | Covert et al. | 294/100 |
| 5,846,489 A | 12/1998 | Bienhaus et al. | 422/63 |
| 5,851,042 A | * 12/1998 | Bankuty et al. | 294/88 |
| 5,855,852 A | 1/1999 | Bienhaus et al. | 422/102 |
| 5,957,822 A | 9/1999 | Bienhaus et al. | 493/100 |
| 6,017,698 A | 1/2000 | Bienhaus et al. | 435/6 |

FOREIGN PATENT DOCUMENTS

| | | |
|---|---|---|
| EP | 0734768 A1 | 10/1996 |
| EP | 0734769 | 10/1996 |
| WO | 9807423 | 11/1998 |

\* cited by examiner

*Primary Examiner*—Dean J. Kramer
(74) *Attorney, Agent, or Firm*—Rankin, Hill, Porter & Clark LLP

(57) ABSTRACT

The invention relates to a lid gripping device for automated handling lids of sample vessels, the lids comprising a spigot to be grasped by the lid gripping device, and the lid gripping device is provided with a collet chuck for grasping the spigot of a lid. The lid gripping device comprises a positioning element for actively actuating the collet chuck, resulting in only minor forces needing to be applied for actuating the lid gripping device, thus permitting application more particularly in robotic devices.

9 Claims, 4 Drawing Sheets

LID GRIPPING DEVICE

The present invention relates to a lid gripping device for automated handling lids of sample vessels, the lids comprising a spigot to be grasped by the lid gripping device, and the lid gripping device is provided with a collet chuck for gripping the spigot of a lid wherein the lid gripping device comprises a positioning element for actively actuating the collet chuck.

Such lidded sample vessels are employed in analytical systems as used in health research, food analysis, environmental analysis, molecular biology and other fields in which contamination of sample substances needs to be reliably avoided. Such vessels and their corresponding lids are known e.g. from DE 44 12 286 A1 and EP 0 734 769 A1.

These lids comprise a cylindrical stopper including a shell wall and a bottom wall. Arranged in the middle of the bottom wall is a vertically protruding spigot by which the lid may be grasped by the lid gripping device. One known lid gripping device (EP 0 734 769 A1, FIG. 7) comprises a collet chuck for gripping the spigot, it functioning according to the principle of a mechanical pencil.

The lid gripping device comprises a tubular housing in a vertical arrangement in which at the lower end a sleeve protruding downwards is shiftingly mounted. Arranged in the sleeve is the collet chuck which is surrounded by a annular element. Shiftingly mounted in the annular element is the collet chuck which opens when shifted downwards by the annular element and closes when shifted upwards in the annular element.

This known lid gripping device functions as follows:

The lid gripping device is mounted from above by its sleeve on a sample vessel. Pressing the lid gripping device downwards urges the sleeve into the housing or lowers the collet chuck together with the annular element within the sleeve so that the collet chuck comes into contact with the spigot. In this action a first spring is tensioned, exerting a first pressure point.

In further pressure from above the collet chuck is urged downwards against the action of a second spring by the annular element so that it opens and is pushed over the spigot.

When a second pressure point is overcome a latching mechanism reduces the pressure exerted downwards by shortening the extent within the lid gripping device, as a result of which the collet chuck grasps the spigot. Since the second spring is still tensioned the annular element is urged downwards and the collet chuck contracted with the spigot clamped therein. Lifting the lid gripping device then removes the lid from the sample vessel.

The latching mechanism is configured similar to that as used in ball pens which latch every time a pressure pulse is applied between an expanded and contracted position respectively.

In mounting the lid on the sample vessel the latching mechanism translates back into its expanded position, as a result of which the collet chuck is urged downwards by the annular element, it opening and releasing the spigot or lid, this requiring a further pressure point to be overcome.

It is intended to use such lid gripping devices in conjunction with automated robotic devices (FIG. 5 of DE 44 12 288 A1).

Setting the forces to be exerted in overcoming the corresponding pressure point has turned out to be difficult, however. Although making the setting with a considerable excess force is basically possible in ensuring reliable actuation of the lid gripping device, this results in the long run in the actuating means of the robotic device being considerably strained and in mechanical distortion of the robotic device in persistent operation which in turn with increasing inaccuracy may result in malfunctioning in gripping or releasing the lids as well as detrimenting other functions of the robotic device.

Disclosed by CH 671 526 A1 is a pipetting device comprising a collet having a pair of arms with which pipettes may be positively grasped at annular beads. For releasing the engagement between the collet and a pipette a spreader sleeve is provided with which the collet may be splayed so that the pipette falls out of engagement. A pipetting device provided with such a collet which holds the pipette solely by its clamping effect fails to be suitable as a gripping device for automated handling sample vessel lids since the lids close off in part very tight and then may only be removed from the sample vessels with great exertion. To enable such high forces to be applied the collet would have to be configured extremely stiff, as a result of which correspondingly high compressive forces would need to be overcome in gripping. It is, however, also possible that the lids may be removed very easily, especially when the lids have already been mounted on a sample vessel several times.

In addition to this the pins for gripping the lids become clogged from frequent handling of the lids thus making a positive grip as needed in the pipetting device impossible in long-term use.

The object of the invention is to provide a lid gripping device for automated handling of sample vessel lids comprising a collet chuck operating on the principle of a mechanical pencil and suitable for use in a robotic device.

This object is achieved by a lid gripping device provided with a collet chuck for gripping the spigot of a lid wherein the lid gripping device comprises a positioning element for actively actuating the collet chuck. Advantageous aspects read from the sub-claims.

The collet chuck of the lid gripping device in accordance with the invention may be actively opened, as a result of which a spigot of a lid may be clasped and grasped by the collet chuck with no compressive force whatsoever.

Reactuating the collet chuck releases the lid from the lid gripping device, again without any pressure point whatsoever needing to be overcome.

In addition, providing an actively actuated collet chuck permits detection of a standby condition in which no lid is grasped and a gripping condition in which a lid is grasped due to the different positions of the collet chuck in the standby condition in which no lid is grasped and a gripping condition in which a lid is grasped.

The invention will now be discussed in more detail by way of example embodiments with reference to the attached drawings in which.

Figure 1:
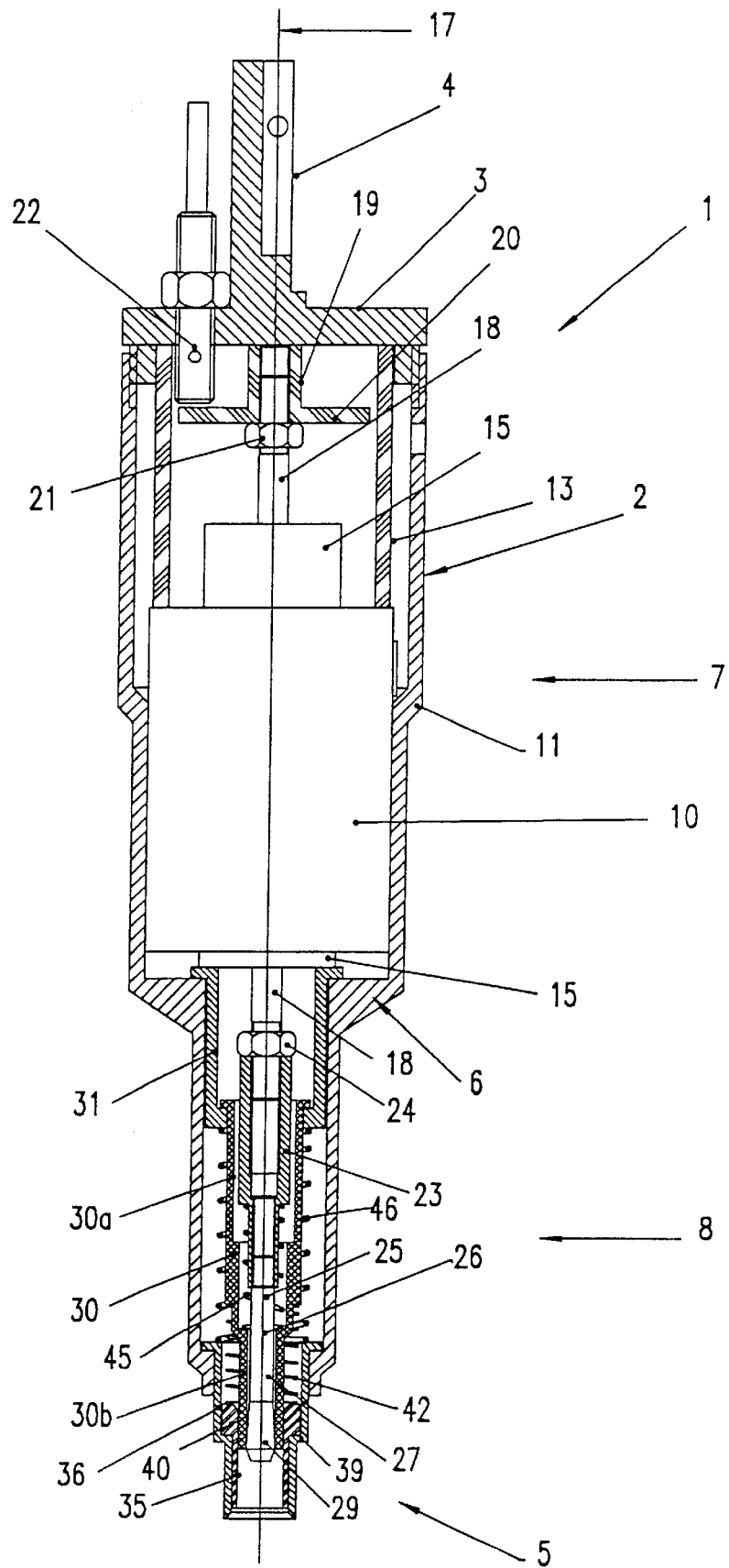
FIG. 1 is cross-section through a lid gripping device.

The lid gripping device 1 in accordance with the invention comprises a tubular housing 2 which is closed off at one end by a housing cover 3. Arranged on the housing cover 3 is a fastener pin 4 protruding outwardly, by means of which the lid gripping device 1 may be secured to an actuating arm of a robotic device, one such robotic device being described for example in German Utility Model Application DE 297 20 432.7.

Since the lid gripping device 1 is employed in a robotic device as a rule with the housing cover 3 facing upwards "upper" or "upwards" as termed in the following description is understood to be in the direction of the housing cover 3 and "lower" or "downwards" in the direction of the free end 5 opposite the housing cover 3. It will, however, be appreciated that the lid gripping device 1 in accordance with the invention is not restricted to this orientation, it permitting arrangement, just as well, horizontally or with its free end 4 facing upwards.

In the direction of the free end 5 of the lid gripping device 1 the housing 2 is configured tapered in steps. Roughly at ⅔rds (starting from the cover 3) of the length of the housing 2 an annular step 6 is provided which reduces the diameter of the housing 2 approximately by half and divides the lid gripping device into an actuating portion 7 configured between the cover 3 and the annular step 6 and a gripping portion 8 extending from the annular step 6 to the free end 5.

Arranged in the relatively voluminous actuating portion 7 is a solenoid 10. The solenoid 10 has the shape of a hollow cylinder and is positively located by its shell surface area on the housing 2 in the lower portion of the actuating portion 7 which as compared to the upper portion is offset by a further small annular step 11. Clamped between the solenoid 10 and the cover 3 is a clamping sleeve 13 which impacts the solenoid 10 from above, urging it in the direction of the annular step 6.

The solenoid 10 comprises a guide sleeve 15 configured integrally with the solenoid 10, this guide sleeve passing through the hollow solenoid 10 and protruding slightly therefrom both upwardly and downwardly. The guide sleeve 15 has a hole drilled in it concentrically to a longitudinal axis 17 of the solenoid 10 and the lid gripping device 1 as a whole.

Located in the hole of the guide sleeve 15 is an actuating rod 18 shiftable along the longitudinal axis 17, this rod protruding from the guide sleeve 15 both upwardly and downwardly. The actuating rod 18 is provided with an armature core (not shown) located within the solenoid 10, this core moving the actuating rod 18 downwards when a current is applied to the solenoid 10.

The actuating rod 18 is provided at each of its end portions with a threaded section. Screwed to the upper threaded section is a tubular stop 19 comprising at its lower rim a peripheral ridge 20. The stop 19 is locked in place by a locknut 21. On stroke actuation of the actuating rod 18 the stop 19 is moved upwards until it comes into contact with the housing cover 3, it thereby defining the maximum stroke of the actuating rod 18. By adjusting the stop 19 on the actuating rod 18 the maximum stroke may be set accordingly.

Inserted in the housing cover 3 is a proximity sensor 22 which detects the ridge 20 of the stop 19 when the latter is in contact with the housing cover 3. Instead of a proximity sensor any other sensor suitable for detecting the stop 19 in contact with the housing cover 3 or a gap between the stop 19 and the housing cover 3 may be used. One such sensor may be configured for example as a photocell, complete bifurcated photocell elements being available for such purposes.

The lower end of the actuating rod 18 extends up to the gripping portion 8. Screwed to the lower threaded section of the actuating rod 18 is a threaded sleeve 23 locked in place by means of a locknut 24. Inserted into the threaded sleeve 23 protruding downwards from the actuating rod 18 is a collet chuck or collet 25 and clamped in place therein. The collet chuck 25 is arranged as an axial extension of the actuating rod 18 concentric to the longitudinal axis 17. The collet chuck 25 is a tube multiply slotted lengthwise upwardly from its lower end, four such slots 26 preferably being provided, between each of which a collet tongue 27 is machined. At the lower end portion each of the collet tongues 27 features a material thickness increasing in the direction of the end so that the outer circumference of the collet chuck 25 is correspondingly increased and this flared portion forming a wedge clamping section 29.

The lower end portion of the actuating rod 18 and of the collet chuck 25 are arranged within a collet 30 and a spacing sleeve 31. The spacing sleeve 31 comprises at its upper rim an annular ridge 32 protruding outwards and at its lower rim an annular ridge 33 protruding inwards. The upper annular ridge 32 protruding outwards clasps the annular step 6 of the housing 2 and is clamped in place between the annular step 6 and the guide sleeve 15 of the solenoid 10. The spacing sleeve 31 is positively in contact with the inner wall of the housing 2 by its shell wall.

The collet 30 comprises a large diameter upper section 30a and a smaller diameter lower clamping section 30b. Configured at the upper rim of the upper section 30a is an annular ridge 30c protruding outwardly. The clamping section 30b surrounds at least the wedge clamping section 29 of the collet chuck 25 when the latter is located in its upper position, i.e. when the stop 19 is in contact with the housing cover 3. The inner diameter of the clamping section 30b of the collet 30 corresponds to the outer diameter of the contracted wedge clamping section 29 at its thickest location.

Figure 2:
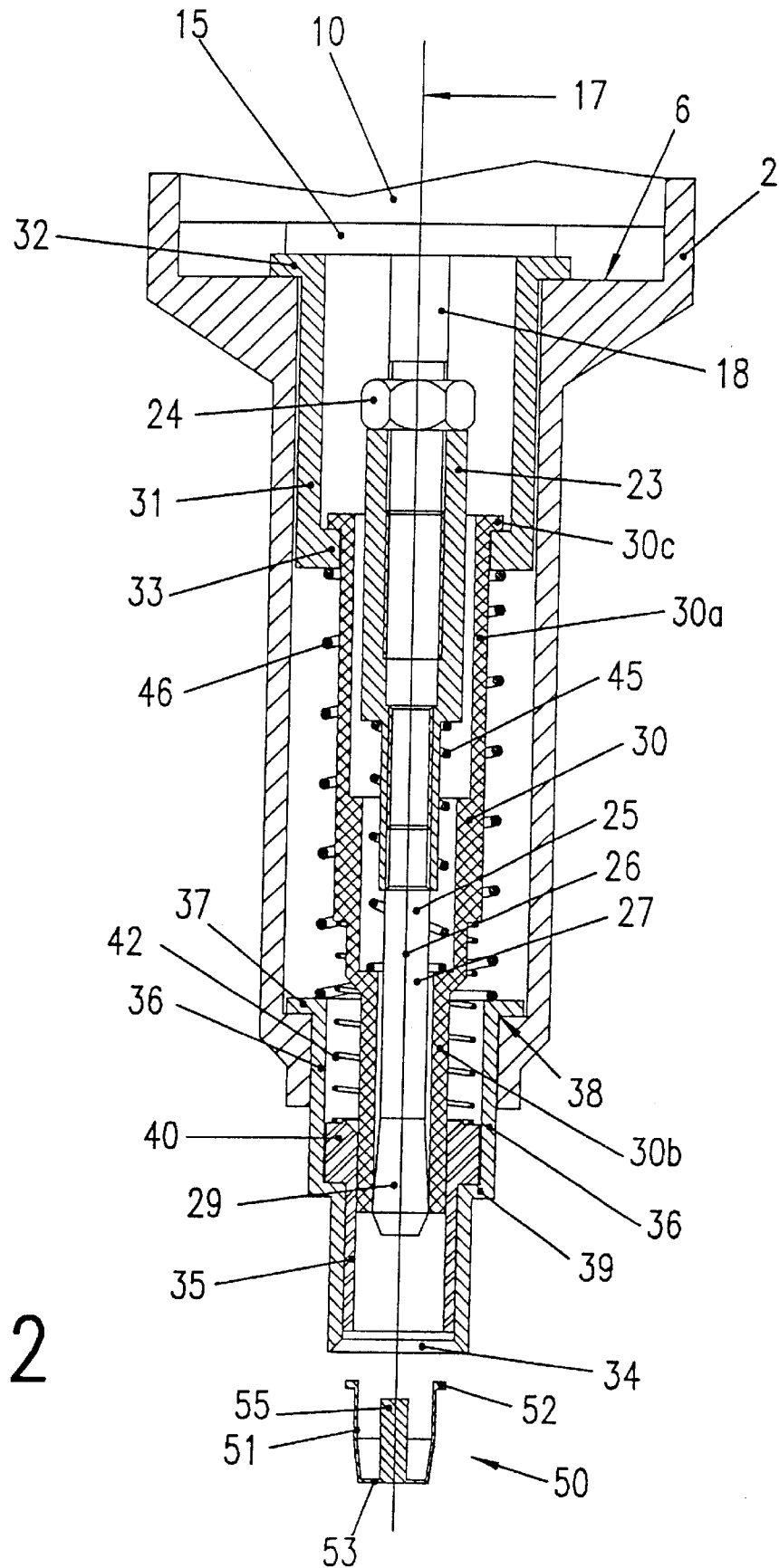
FIG. 2 is a cross-section through the free end portion of the lid gripping device as shown in FIG. 1 in the standby condition.

The lower end of the collet 30 is mounted in a sweeper sleeve 35 which is in turn arranged in a hold-down sleeve 36. The hold-down sleeve 36 comprises at its upper rim an annular ridge 37 protruding outwardly surrounding an annular edge 38 at the lower end of the housing 2 (see FIG. 2). The lower rim of the hold-down sleeve 36 is face chamfered to form a lead-in ramp 34.

The hold-down sleeve 36 is positively located by its shell surface area in contact with the portion of the housing 2 protruding downwards from the annular edge 38. The hold-down sleeve 36 comprises roughly midway a doubled right-angled annular step 39, the portion below the annular step 39 having a smaller diameter than the portion above the annular step.

The sweeper sleeve 35 is configured at its upper rim with an annular ridge 40 protruding outwardly, clasping the annular step 39 of the hold-down sleeve 36. The sweeper sleeve 35 is positively located by its shell surface area in contact with the inner surface area of the hold-down sleeve 36 in the portion below the annular step 39 and is mounted vertically shiftable in the hold-down sleeve 36.

The sweeper spring 42 is clamped in place between the annular element 40 in the sweeper sleeve 35 and an annular edge 43 at the collet 30 so that the sweeper sleeve 35 is urged with its annular element 40 against the annular step 39 of the hold-down sleeve 36.

A return spring 45 is arranged within the collet 30 between two annular edges configured on the threaded sleeve 23 and on the collet 30 so that the collet 30 is urged downwardly to firmly engage the lower annular ridge 33 of the spacing sleeve 31 or urging the threaded sleeve 23 together with the actuating rod 18 and the collet chuck 25 upwardly against the housing cover 3.

Provided in the chamber between the collet 30 and the housing 2 is a further helical spring—the hold-down spring 46—which is clamped in place between the lower annular ridge 33 of the spacing sleeve 31 and the annular ridge 37 of the hold-down sleeve 36 and urging the hold-down sleeve 36 downwards against the annular edge 38 of the housing 2.

The hold-down spring 46 is dimensioned such that when the lid gripping device 1 is pressed down onto the vessel containing the lid to be removed, the force exerted by the hold-down sleeve 36 is greater than the frictional force between the lid and the vessel thus assuring that on extracting the lid from the vessel the vessel is not including in extraction, it instead being held down by the hold-down sleeve 36.

The functioning of the lid gripping device in accordance with the invention will now discussed.

The lid gripping device 1 is mounted by a downwards movement onto the vessel (not shown) closed off by a lid 50. The lid 50 comprises a shell wall 51 provided at its upper rim with an annular ridge 52 oriented outwardly. At the lower rim of the shell wall 51 the lid 50 is provided with a bottom wall 53. Arranged in the middle of the bottom wall 53 is an upwardly protruding spigot 55.

In mounting the lid gripping device 1 on the lid 50 the latter is guided along the guide-in ramp 34 into the hold-down sleeve 36, the annular ridge 52 of the lid 50 urging the sweeper sleeve 35 upwards against the action of the sweeper spring 42.

Once the lid 50 is in the receiving portion of the gripping device 1, i.e. in the lower portion of the hold-down sleeve 36 the solenoid 10 is signalled by a current pulse, as a result of which the actuating rod 18 is shifted downwards, causing the collet chuck 25 to be run downwards by its clamping wedge section 29 from the collet 30 and open since it is no longer clamped in place by the clamping section 30b. The collet tongues 27 clasp the spigot 55 of the lid 50.

The point in time at which the current pulse is applied to actuate the gripping device 1 is dictated by the robotic device as a function of the height of the actuating arm of the robotic device carrying the lid gripping device 1.

The solenoid 10 is signalled OFF as a result of which the actuating rod 18 together with the threaded sleeve 23 and the collet chuck 25 are urged upwards by the action of the return spring 45, the collet chuck 25 thereby being drawn into the clamping section 30b and the collet tongues 27 contracted with the spigot 55 located in between. The spigot 55 is firmly grasped by friction action with the collet tongues 27 and the lid 50 fully drawn into the receiving portion of the lid gripping device 1. The lid 50 is then totally removed from the vessel by the lid gripping device being lifted, the hold-down sleeve 36 holding down the vessel to prevent it from being included in the lifting action.

Figure 3:
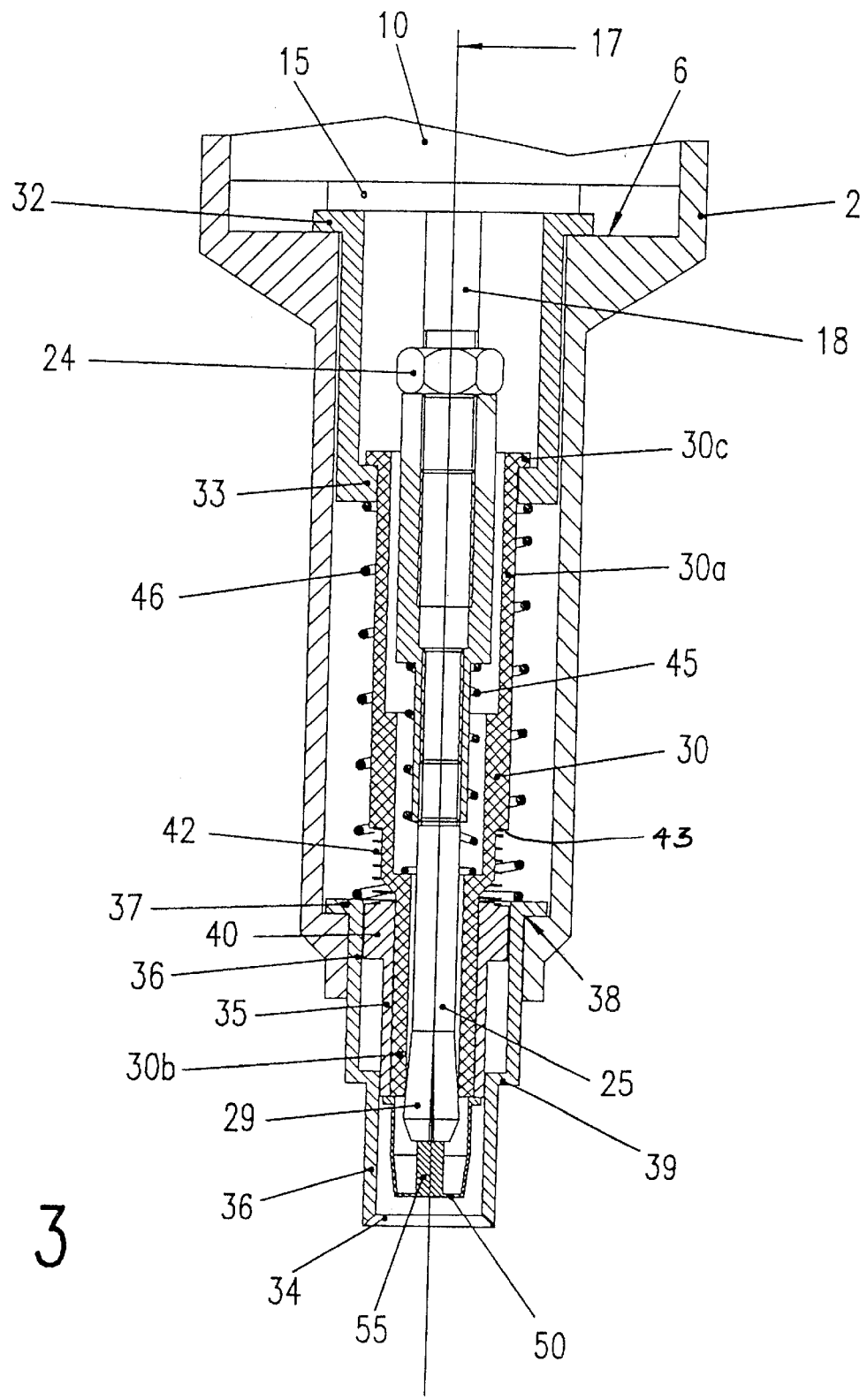
FIG. 3 is a cross-section through the free end portion of the lid gripping device as shown in FIG. 1 in the gripping condition.

The lid gripping device 1 is then in a gripping condition (FIG. 3) in which the stop 19 is arranged spaced away from the proximity sensor 22. This spacing is sensed by the proximity sensor 22 and "seen" as the gripping condition of the lid gripping device 1.

In closing the vessel the lid gripping device 1 is mounted on the vessel with the lid 50 in the receiving portion, the lid 50 being inserted by its shell walls 51 into the tubular vessel. The solenoid 10 is signalled by a current pulse, as a result of which the collet chuck 25 is retracted from the clamping section 30b by its wedge clamping section 29 and opened, as a result of which the lid 50 is released. The lid gripping device is then removed from the vessel with its solenoid 10 ON, the sweeper sleeve 35 sweeping the lid 50 from the receiving portion of the gripping device 1 by the action of the sweeper spring 42.

After removal of the lid gripping device 1 from the vessel the solenoid 10 is signalled OFF, as a result of which the lid gripping device is returned to its standby condition (FIGS. 1, 2) in which the stop 19 is in contact with the housing cover 3. In this standby condition the peripheral rim 20 of the stop 19 is in contact with the proximity sensor 22, this being "seen" by the proximity sensor 22 as the standby condition.

Since gripping in the case of the lid gripping device 1 in accordance with the invention is carried out actively by a positioning element (solenoid 10) and not passively via signal control by means of several pressure points a lid may be mounted or removed on/from a sample vessel with minimum robotic device forces. In addition the lid gripping device 1 in accordance with the invention permits monitoring the standby condition and the gripping condition so that e.g. any gripping action having occurred incorrectly may be "seen" and instantly repeated. How often this is repeated is preferably dictated by a predetermined value so that the working program of the robotic device is not held up by an error in gripping a lid (e.g. defective spigot, lid missing).

The three-dimensional shape of the receiving portion is to be adapted to the lid to be handled and the invention is thus not restricted to the three-dimensional shape as depicted in the example embodiment. What is important for the invention is that the collet chuck is actively actuated by a positioning element so that no additional forces are needed from without.

The lid gripping device in accordance with the invention thus provides the positioning element in the form of the solenoid 10 for actuating the return spring 45 which is the hardest of the three springs arranged in the gripping portion 8, as a result of which the force to be applied by the robotic device—for actuating the sweeper spring 42 and the hold-down spring 46—is considerably reduced.

Instead of the proximity sensor the standby condition and gripping condition may also be "seen" from a change in the inductance of the solenoid prompted by the position of the actuating rod or the armature body thereof in the solenoid.

Figure 4:
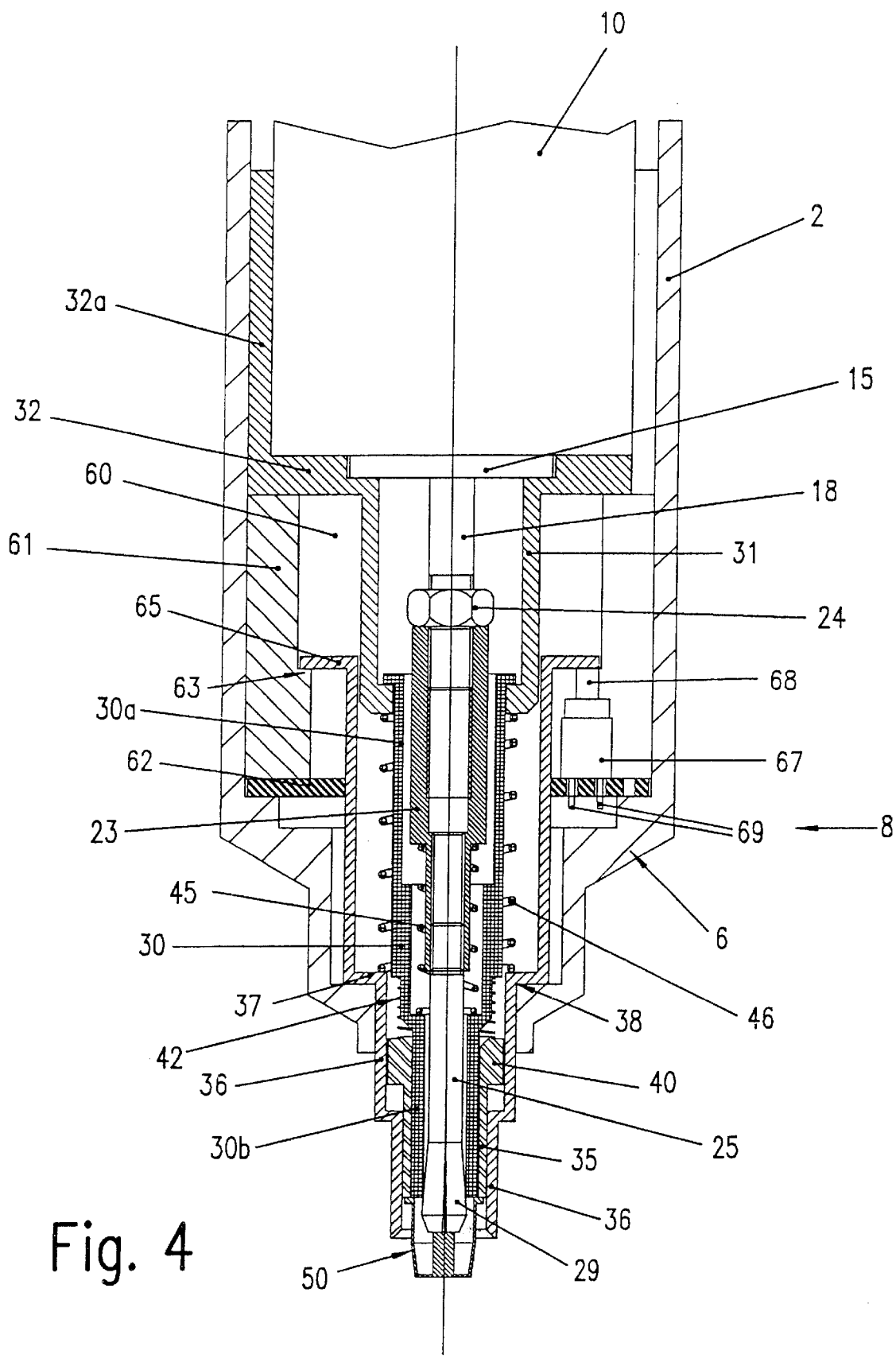
FIG. 4 is a cross-section through the free end portion of a further lid gripping device in the gripping condition.

In FIG. 4 the free end portion of a second example embodiment of a lid gripping device is shown in cross-section. The actuating portion of this lid gripping device 1 is identical to the actuating portion 7 of the lid gripping device as described above. The two lid gripping devices differ merely in the gripping portion 8. Since many parts of the two lid gripping devices are identical, like parts are identified by like reference numerals.

The second example embodiment of the lid gripping device 1 comprises in turn a housing 2, a solenoid 10, a collet chuck 25 secured by means of a threaded sleeve 23 to an actuating rod actuated by the solenoid, a sweeper sleeve 35, a hold-down sleeve 36, a collet 30 comprising an upper section 30a and a clamping section 30b cooperating with the wedge clamping section 29 of the collet chuck, a spacing sleeve 31 and the corresponding helical springs (sweeper spring 42, return spring 45, hold-down spring 46).

In the second example embodiment the annular step 6, at which the diameter of the housing 2 is reduced roughly by half, is arranged roughly midway in the gripping portion 8, as a result of which as compared to the first example embodiment an additional cavity 60 is created between the lower edge of the solenoid 10 and the annular step 6. To define this cavity 60 a tubular, vertical slotted spacer bush 61 is provided which is in contact with the inner wall of the housing 2. The lower rim of the spacer bush 61 is in contact with the annular disk 62 which in turn is seated on the annular step 6. The upper rim of the spacer bush 61 is clasped by the spacing sleeve 31, the annular ridge 32 of which extends radially outwards up to the inner wall of the housing 2. The spacing sleeve 31 is elongated at the outer rim of the annular ridge 32 upwardly by a cylindrical sleeve section 32a which clasps the lower portion of the solenoid 10 and is provided with a vertical slot (on the right in FIG. 4). Machined from the inner wall of the spacer bush 61 is an annular edge 63 undercut upwardly.

The hold-down sleeve 36 in turn clasps by its annular ridge 37 the annular rim 38 of the housing 2 and is elongated from the outer rim of the annular ridge 37 upwardly through the annular disk 62 into the cavity 60 and provided at its upper end with a further annular ridge 65 protruding radially outwards which clasps the annular rim 63 of the spacer bush 61.

Arranged between the annular disk 62 and the annular ridge 65 of the hold-down sleeve 36 is a microwswitch 67 adjoining the slotted portion of the spacer bush. The microwswitch 67 comprises a feeler element 68 which is actuated by the annular ridge 65 of the hold-down sleeve 36. The annular disk 62 is provided with two vertical through-holes locating two terminals 69 of the microwswitch 67. The terminals 69 are electrically connected to the circuit (not shown) for energizing the solenoid 10 via a control logic which directly signals control of the solenoid 10 by means of a power transistor.

When the hold-down sleeve 37 is urged downwards by the action of the hold-down spring 46 in contact with the annular rim 38 by its annular ridge 37 or in contact with the annular rim 62 by its annular ridge 65 then the feeler element 68 is advanced into the microwswitch 67. When the hold-down sleeve 36 is shifted upwards against the action of the hold-down spring 46 the feeler element 68 is released.

The microwswitch 67 is coupled to the control electronics in such a way that when the feeler element 68 is advanced the circuit to the solenoid 10 is open and when the feeler element 68 is released the circuit is closed. The microwswitch 67 thus detects the position of the hold-down sleeve 36 for signalling control of the solenoid 10.

The functioning of this lid gripping device is substantially the same as that of the first example embodiment, except that the current pulse is activated by the microwswitch 37 on both opening and closing the vessel. When the vessel is opened, i.e. when the lid 50 is removed from the vessel, the current pulse is open-circuited by the control means roughly at the lowest position of the lid gripping device above the vessel. When the vessel is closed, i.e. when mounting the lid on the vessel, the current pulse energizing the solenoid 10 can only be signalled by the microwswitch 67, meaning that as long as the hold-down sleeve 36 is inserted in the housing 2 the solenoid is energized and the collet chuck 25 urged downwards so that a spigot 55 of a lid 50 clamped by the collet chuck is released.

This control by means of a microwswitch permits straightforward signal control of the lid gripping device, in addition independently of the height at which the vessels to be opened or closed are arranged.

In addition to this, the microwswitch 67 permits detecting whether the lid gripping device is seated on the vessel to be opened or closed, this being a significant checking function which enhances reliable functioning and represents a substantial advantage when the working routines to be implemented by the robotic device are lengthy procedures.

This also makes it possible to "see" whether a lid 50 to be grasped is missing. For this purpose it is established by the sensor 22—following one or more vain attempts to grip a lid—that not the gripping condition but the standby condition exists, so that a new lid 50 is picked from the lid reservoir. An attempt is then made to place this lid 50 in the vessel. If this is successful the new lid is treated as the lid assigned to the vessel and the working routine to be implemented by the robotic device continues with no change. Should despite vain grip attempts a lid actually exit in the vessel the new lid cannot be inserted in the vessel. This result in the new lid being returned to the lid reservoir and an alarm is output.

In one simplified method having no lid reservoir the robotic device is halted after a few (e.g. 3 to 5) vain attempts to grip a lid and an alarm is output. The user can then elect to either cause the robotic device to ignore the "alarm" and to sequence its working routine with no change, or to halt the robotic device.

The invention is discussed above on the basis of an example embodiment having a positioning element configured as a solenoid. It will be appreciated, however, that the invention is not restricted to the positioning element being a solenoid; instead the positioning element may also be devised as a piezo-positioning element or as a linear motor or any other type of positioning element suitable for executing a linear movement.

What is claimed is:

1. A lid gripping device for automated handling lids of sample vessels, said lids comprising a spigot to be grasped by said lid gripping device, said lid gripping device comprising a collet chuck for grasping the spigot of a lid at a free end of said lid gripping device and a positioning element for actively actuating said collet chuck, said collet chuck comprising a wedge clamping section which in a standby condition of said lid gripping device is mounted contracted in a clamping section and in an opening or gripping condition of said lid gripping device is moved partly from said clamping section, said lid gripping device further comprising a sensor for detecting said standby condition in which no lid is grasped and for detecting said gripping condition in which a lid is grasped, wherein said positioning element is a solenoid which in the ON condition moves said collet chuck with its wedge clamping section from said clamping section contracting said collet chuck and said solenoid for actuating said collet chuck is a component of said sensor.

2. The lid gripping device as set forth in claim 1 wherein said clamping section is a component of a collet in which a return spring is arranged so that said collet is urged in the direction of the free end of said lid gripping device and a unit consisting of said collet chuck and an actuating rod is urged away from said free end.

3. The lid gripping device as set forth in claim 2 wherein said lid gripping device comprises a roughly tubular housing, at the end of which facing said free end of said lid gripping device a hold-down sleeve is arranged protrudingly, said hold-down sleeve being shiftable into said housing against the action of a hold-down spring.

4. The lid gripping device as set forth in claim 3 wherein a microwswitch is provided to detect the position of said hold-down sleeve.

5. The lid gripping device as set forth in claim 4 wherein said microswitch is included in a circuit that controls said solenoid, said circuit being opened in the position of when said hold-down sleeve is not shifted into said housing.

6. The lid gripping device as set forth in claim 5 wherein said clamping section is surrounded by a sweeper sleeve protruding from said clamping section in the direction of said free end and shiftable onto said clamping section against the action of a sweeper spring.

7. The lid gripping device as set forth in claim 6 attached to a robotic device.

8. A lid gripping device for automated handling lids of sample vessels, said lids comprising a spigot to be grasped by said lid gripping device, said lid gripping device comprising a collet chuck for grasping the spigot of a lid at a free end of said lid gripping device and a positioning element for actively actuating said collet chuck, said collet chuck comprising a wedge clamping section which in a standby condition of said lid gripping device is mounted contracted in a clamping section and in an opening or gripping condition of said lid gripping device is moved partly from said clamping section, wherein said clamping section is a component of a collet in which a return spring is arranged so that said collet is urged in the direction of the free end of said lid gripping device and a unit consisting of said collet chuck and an actuating rod is urged away from said free end.

9. A lid gripping device for automated handling lids of sample vessels, said lids comprising a spigot to be grasped by said lid gripping device, said lid gripping device comprising a collet chuck for grasping the spigot of a lid at a free end of said lid gripping device and a positioning element for actively actuating said collet chuck, wherein said lid gripping device comprises a roughly tubular housing, at the end of which facing said free end of said lid gripping device a hold-down sleeve is arranged protrudingly, said hold-down sleeve being shiftable into said housing against the action of a hold-down spring, and wherein a microswitch is provided to detect the position of said hold-down sleeve.

* * * * *